United States Patent [19]
Bank et al.

[11] Patent Number: 5,914,421
[45] Date of Patent: Jun. 22, 1999

[54] METHOD FOR PREPARATION OF ALKOXYSILANES HAVING REDUCED HALIDE CONTENT

[75] Inventors: Howard Marvin Bank, Freeland; Robert James Cyr; Binh Thanh Nguyen, both of Midland; Emmanuel Babatunde, Grand Blanc, all of Mich.

[73] Assignee: Dow Corning Corporation, Midland, Mich.

[21] Appl. No.: 09/108,625

[22] Filed: Jul. 1, 1998

[51] Int. Cl.$^6$ .................................................. C07F 7/08
[52] U.S. Cl. .................................................. 556/466
[58] Field of Search ............................................. 556/466

[56] References Cited

U.S. PATENT DOCUMENTS

| | | | |
|---|---|---|---|
| 2,698,861 | 1/1955 | Shorr | 260/448 |
| 4,281,146 | 7/1981 | Ashby | 556/456 |
| 4,697,027 | 9/1987 | Sugihara et al. | 556/466 |
| 4,732,996 | 3/1988 | Moorhead et al. | 556/466 |
| 4,827,008 | 5/1989 | Gousetis et al. | 556/466 |
| 5,084,588 | 1/1992 | Ocheltree et al. | 556/466 |
| 5,104,999 | 4/1992 | Satoh | 556/466 |
| 5,210,254 | 5/1993 | Ritscher et al. | 556/466 |
| 5,247,117 | 9/1993 | Yamazaki et al. | 556/466 |
| 5,260,470 | 11/1993 | Goebel et al. | 556/466 |

*Primary Examiner*—Paul F. Shaver
*Attorney, Agent, or Firm*—Melvin D. Fletcher

[57] ABSTRACT

A method of preparing an alkoxysilane having reduced halide content. The method comprises contacting a mixture comprising an alkoxysilane and residual halide with a mixture comprising about 1.5 to 15 moles of an alkyl alcohol per mole of residual halide, the alkyl alcohol comprising 1 to about 4 carbon atoms and about 0.1 to 5 moles of an orthoformate per mole of residual halide, to form a mixture comprising additional alkoxysilane and lower boiling species, and separating the lower boiling species and the alkoxysilane. Remaining residual halide may be contacted alkali metal to further reduce the halide content. Alkoxysilanes are useful as catalyst modifiers to manufacture polypropylene.

20 Claims, No Drawings

5,914,421

METHOD FOR PREPARATION OF ALKOXYSILANES HAVING REDUCED HALIDE CONTENT

BACKGROUND OF INVENTION

The present invention is a method of preparing an alkoxysilane having reduced halide content. The method comprises contacting a mixture comprising an alkoxysilane and residual halide with a mixture comprising about 1.5 to 15 moles of an alkyl alcohol per mole of residual halide, the alkyl alcohol comprising 1 to about 4 carbon atoms and about 0.1 to 5 moles of an orthoformate per mole of residual halide, to form a mixture comprising additional alkoxysilane and lower boiling species, and separating the lower boiling species and the alkoxysilane. Remaining residual halide may be contacted alkali with metal to further reduce the halide content. Alkoxysilanes are useful as catalyst modifiers to manufacture polypropylene.

Shorr, U.S. Pat. No. 2,698,861, describes a method of preparing alkoxysilicon compounds comprising reacting a halosilicon compound selected from the group consisting of halosilanes and partial hydrolyzates with an orthoformate. The by-products of the reaction are an alkyl halide, residual halide species, and a formic acid ester.

Ashby, U.S. Pat. No. 4,281,146, describes a method of neutralizing a halogen silicone compound comprising adding to the halogen silicone compound an orthoformate and an alcohol to form an alkyl chloride and a formate which can then be distilled off. The method uses excess trimethylorthoformate to neutralize the halogen silicone compound which is expensive and undesirable on a commercial scale.

The present invention provides a method for reducing the halide content of alkoxysilanes. In addition, a method is provided to reduce the residual halide content of alkoxysilanes while reducing alkali metal salt formation and filtration cycle time. Furthermore, the invention provides a method for reducing the halide content of sterically hindered alkoxysilanes.

SUMMARY OF INVENTION

The present invention is a method of preparing an alkoxysilane having reduced halide content. The method comprises contacting a mixture comprising an alkoxysilane and residual halide with a mixture comprising about 1.5 to 15 moles of an alkyl alcohol per mole of residual halide, the alkyl alcohol comprising 1 to about 4 carbon atoms and about 0.1 to 5 moles of an orthoformate per mole of residual halide, to form a mixture comprising additional alkoxysilane and lower boiling species, and separating the lower boiling species and the alkoxysilane.

DESCRIPTION OF INVENTION

The present invention is a method for preparation of alkoxysilanes having reduced halide content. The method comprises contacting a mixture comprising an alkoxysilane described by formula $R_aH_bSi(OR^1)_{(4-a-b)}$, and residual halide with a mixture comprising about 1.5 to 15 moles of an alkyl alcohol per mole of residual halide, the alkyl alcohol comprising 1 to about 4 carbon atoms and about 0.1 to 5 moles of an orthoformate described by formula $HC(OR^1)_3$ per mole of residual halide, where each R is independently selected from the group consisting of substituted and unsubstituted hydrocarbon groups comprising 1 to about 20 carbon atoms, each $R^1$ is an independently selected hydrocarbon group comprising 1 to 4 carbon atoms, a=0, 1, 2, or 3, b=0, 1, 2, or 3, and a+b=0 to 3, to form a mixture comprising additional alkoxysilane and lower boiling species, and separating the lower boiling species and the alkoxysilane.

Contacting the mixture comprising an alkoxysilane and residual halide with mixture comprising an alkyl alcohol and an orthoformate can be effected in standard type reactors for conducting alkoxylation reactions. The reactor can be of a batch type, semi-batch type, or continuous type.

The alkoxysilanes of the method are described by formula $R_aH_bSi(OR^1)_{(4-a-b)}$, where each R is independently selected from the group consisting of substituted and unsubstituted hydrocarbon groups comprising 1 to about 20 carbon atoms, a=0, 1, 2, or 3, and b=0, 1, 2, or 3, and a+b=0 to 3. R can be an alkyl group, such as, methyl, ethyl, propyl, butyl, pentyl, and hexyl; an alkenyl group, such as, vinyl, allyl and hexenyl; a cycloalkyl group, such as, cyclopropyl, cyclobutyl, cyclopentyl, dicyclopentyl, and cyclohexyl; a cycloalkenyl group, such as, cyclobutenyl, cyclopentenyl and cyclohexenyl; an aryl group, such as, phenyl, tolyl and naphthyl. Specific examples of alkoxysilanes include methoxysilane, ethoxysilane, butoxysilane, dimethyldimethoxysilane, trimethoxysilane, dimethoxysilane, t-butyltrimethoxysilane, t-butylmethyldimethoxysilane, tert-butyltrimethoxysilane, dimethyldiethoxysilane, phenyltriethoxysilane, octadecylvinyldimethoxysilane, phenylmethyldiethoxysilane, diphenyldimethoxysilane, isobutyltrimethoxysilane, octadecyltrimethoxysilane, cyclohexylmethyldimethoxysilane, triethoxysilane, methylvinyldimethoxysilane, triphenylmethoxysilane, 2-phenylpropylmethyldimethoxysilane, methylhexadienyldimethoxysilane, (chloropropyl) trimethoxysilane, (3,3,3-trifluoropropyl)trimethoxysilane, bis-(3,3,3-trifluoropropyl)dimethoxysilane, dicyclopentyldimethoxysilane, dodecyltrimethoxysilane, 5-hexenyldimethylmethoxysilane, and tris-(3,3,3-trifluoropropyl)methoxysilane. The preferred alkoxysilanes are dicyclopentyldimethoxysilane and cyclohexylmethyldimethoxysilane.

The residual halide present in the mixture is a by-product of reacting a halosilane with alcohol, where the residual halide is in the form of halosilanes and hydrogen chloride. The hydrochloric acid may be easily separated by distillation, however the residual halide in the form of halosilanes are not easily separated by distillation because their boiling points are close to that of the alkoxysilanes. The residual halides may include, for example, dimethylchloroethoxysilane, phenylmethylmethoxychlorosilane, dicyclopentylchloromethoxysilane, phenylfluorodiethoxysilane, cyclohexylmethylchloromethoxysilane, and mixtures of residual halides. It is desirable to reduce the amount of residual halide in the mixture because it may cause the final product to be acidic and lead to the product reverting or degrading upon standing.

Alternatively, the residual halide may be contacted with a metal alkoxide to form an alkali metal salt. However, this route is undesirable because the result is a high alkali metal salt formation resulting in long filtration cycle time. Thus, it is much more economically desirable to reduce the residual halide by, for example, distillation before filtration, otherwise the filtration cycle time may be more than doubled.

The mixture comprising an alkoxysilane and residual halide is contacted with a mixture comprising about 1.5 to 15 moles of an alkyl alcohol comprising 1 to about 4 carbon atoms per mole of residual halide and about 0.1 to 5 moles of an orthoformate per mole of residual halide to form a mixture comprising additional alkoxysilane and lower boiling species. Preferably, the mixture comprises about 2.5 to 10 moles of alkyl alcohol comprising 1 to about 4 carbon atoms per mole of residual halide. Most preferably, the mixture comprises about 3.5 to 7 moles of alkyl alcohol comprising 1 to about 4 carbon atoms per mole of residual halide. Specific examples of alkyl alcohols useful in the method include methanol, ethanol, propanol, and butanol. Preferred alkyl alcohols are methanol and ethanol.

The mixture further comprises about 0.1 to 5 moles of an orthoformate described by formula $HC(OR^1)_3$ per mole of residual halide. Preferably, the mixture comprises about 0.5 to 2 moles of orthoformate per mole of residual halide. Most preferably the mixture comprises a stoichiometric amount of orthoformate per mole of residual halide. Each $R^1$ is an independently selected hydrocarbon group comprising 1 to 4 carbon atoms. Preferably $R^1$ is methyl or ethyl. Specific examples of orthoformates are trimethyl orthoformate, and triethyl orthoformate. Preferred are trimethyl orthoformate and triethyl orthoformate.

In the preferred embodiment of the method the orthoformate is dissolved in the alkyl alcohol. Preferred is when the weight percent of the orthoformate in alkyl alcohol is in the range of about 10 to 60 weight percent. More preferred is when the weight percent of orthoformate in alkyl alcohol is in the range of about 20 to 50 weight percent. Most preferred is when the weight percent of orthoformate in alkyl alcohol is in the range of about 25 to 30 weight percent. It was discovered that in this range, that the weight percent of orthoformate to alkyl alcohol resulted in significant economical savings in the amount of orthoformate used, while significantly decreasing residual halide reduction.

When the mixture comprising an alkoxysilane and residual halide is contacted with the mixture comprising an alkyl alcohol and orthoformate, the halide ion attached to the residual halide is alkoxylated to form additional alkoxysilane, as previously described, and lower boiling species. For example, when a mixture comprising methanol and trimethyl orthoformate contacts the residual halide, the halide ion is replaced with a methoxy group to form a methoxysilane and lower boiling species.

The lower boiling species produced by the method include hydrogen chloride; alkylhalides, such as, methylchloride and ethylchloride; residual alkyl alcohols, such as, methanol and ethanol; formic esters; and remaining residual halide. The alkoxysilane can be separated from the lower boiling species by, for example, distillation.

The method is capable of reducing an alkoxysilane residual halide content from about 70,000 ppm to 5 ppm. The residual halide content of the alkoxysilanes may be further reduced to 0 to less than 5 ppm by contacting the lower boiling species with a metal alkoxide to convert any remaining residual halide in the form of halosilane to alkali metal salt. Since the remaining residual halide level was reduced significantly, the concentration of the alkali metal salt formed is low and the resulting alkali metal salt may be separated from the alkoxysilane by, for example, filtration. Under these conditions, the filtration cycle time is minimum and has little effect on overall process time and production cost.

The metal alkoxides useful in the method are sodium methoxide, sodium ethoxide, magnesium oxide, titanium alkoxide, and zirconium alkoxide.

In alternative embodiments of the present method, the mixture comprising the alkoxysilane and residual halide may be contacted with an alkali metal before the mixture is contacted with the orthoformate. Also the alkoxysilane may be contacted with an alkali metal before the lower boiling species are separated from the alkoxysilanes. However, in both cases more alkali metal salts are produced requiring longer filtration cycle time.

The present method can be run at a temperature within a range of about 50° C. to 100° C. It is preferred that the method be run at a temperature within a range of about 70° C. to 85° C.

The following examples are provided to illustrate the present method. The examples are not intended to limit the scope of the present claims.

EXAMPLE 1

Evaluation to reduce residual chloride in cyclohexylmethyldimethoxysilane. A mixture comprising cyclohexylmethyldimethoxysilane and residual chloride 1.8% (0.0005 moles) measured as HCl was loaded into a glass flask equipped with a reflux condenser, heating mantle, and nitrogen inlet port. The initial chloride level was determined to be 18,000 ppm by KOH titration using bromcresol purple (BCP) as an indicator. Based on the acidity results, the mixture was treated with a mixture comprising stoichiometric amounts of 0.05 parts trimethyl orthoformate (0.00051 moles) and 0.16 parts methanol (0.0051 moles). The mixture comprising methanol and trimethyl orthoformate was added through an additional funnel in 0.02 part incremental intervals as the mixture comprising cyclohexylmethyldimethoxysilane was heated to about 80° C. to 85° C. Samples were taken at 1 hour intervals and the chloride level determined by KOH titration using BCP as an indicator. The residual chloride level decreased from 18,000 ppm to 958 ppm in 2.8 hours and after 5.5 hours the residual chloride level decreased to 528 ppm. After 5.5 hours additional trimethyl orthoformate was added to the mixture comprising 0.162 parts methanol and 0.05 parts trimethyl orthoformate. After 7.5 hours the residual chloride level decreased to 126 ppm.

EXAMPLE 2

Evaluation to reduce residual chloride in cyclohexylmethyldimethoxysilane. A mixture comprising cyclohexylmethyldimethoxysilane and residual chloride 1.9% (0.0005 moles) measured as HCl was loaded into a glass flask equipped with a reflux condenser, heating mantle, and nitrogen inlet port. The initial chloride level was determined to be 19,339 ppm by KOH titration using bromcresol purple (BCP) as an indicator. Based on the acidity results, the mixture was treated with a mixture comprising about 0.17 parts methanol (0.0055 moles) and 0.06 parts trimethyl orthoformate (0.00055 moles). The mixture comprising methanol and trimethyl orthoformate was added through an additional funnel in 0.02 part incremental intervals to the mixture comprising cyclohexylmethyldimethoxysilane and residual chloride, and the mixture heated to about 80° C. to 85° C. Samples were taken at 1 hour intervals and the chloride level determined by KOH titration using BCP as an indicator. After 3 hours the mixture comprising methanol and trimethyl orthoformate was adjusted such that the weight percent of the trimethyl orthoformate was 25 weight percent in methanol. The residual chloride level decreased from 19,339 ppm to 528 ppm in 3 hours. A mixture comprising cyclohexylmethyldimethoxysilane and lower boiling species was contacted with sodium methoxide 0.0001 parts to decrease the residual chloride level to less than 5 ppm.

EXAMPLE 3

Evaluation to reduce residual chloride in dicyclopentyldimethoxysilane. A mixture comprising dicyclopentyldimethoxysilane and a monochlorinated silane as $(C_5H_9)_2SiCl(OMe)$ (0.0018 moles) was loaded into a glass flask equipped with a reflux condenser, heating mantle, and nitrogen inlet port. The initial chloride level was determined to be 66,802 ppm by KOH titration using bromcresol purple (BCP) as an indicator. Based on the acidity results, the mixture was treated with a mixture comprising 0.6 parts methanol (0.02 moles) and 0.21 parts trimethyl orthoformate (0.002 moles). The mixture comprising methanol and trimethyl orthoformate was added through an additional funnel in 0.02 part incremental intervals as the mixture comprising dicyclopentyldimethoxysilane was heated to about 80° C. to 85° C. Samples were taken at 1 hour intervals and the chloride level determined by KOH titration using BCP as an indicator. The residual chloride level decreased from 66,802 ppm to 99 ppm in 4 to 6 hours. The mixture comprising dicyclopentyldimethoxysilane and lower boiling species was contacted with sodium methoxide 0.00016 parts to decrease the residual chloride level to less than 5 ppm.

EXAMPLE 4

Evaluation to reduce residual chloride in cyclohexylmethyldimethoxysilane without methanol and excess trimethyl orthoformate. A mixture comprising cyclohexylmethyldimethoxysilane and a monochlorinated silane as $C_6H_{11}MeSiClOMe$ (0.0005 moles) was loaded into a glass flask equipped with a reflux condenser, heating mantle, and nitrogen inlet port. The initial chloride level was determined to be 19,339 ppm by KOH titration using bromcresol purple (BCP) as an indicator. Based on the acidity results, the mixture was treated with a mixture comprising 0.25 parts trimethyl orthoformate (0.02 moles). The trimethyl orthoformate was added through an additional funnel in 0.02 part incremental intervals as the mixture comprising cyclohexylmethyldimethoxysilane and monochlorinated silane was heated to about 80° C. to 85° C. In this amount trimethyl orthoformate was used in about 342% excess. Samples were taken at 1 hour intervals and the chloride level determined by KOH titration using BCP as an indicator. The residual chloride level decreased from 19,339 ppm to 1,023 ppm in 5 hours. The residual chloride level in the mixture was further reduced to 38 ppm by adding 0.06 parts methanol (0.002 moles).

EXAMPLE 5

Evaluation to reduce residual chloride in cyclohexylmethyldimethoxysilane with a stoichiometric amount of trimethyl orthoformate. A mixture comprising cyclohexylmethyldimethoxysilane and monochlorinated silane as $C_6H_{11}MeSiClOMe$ 1.8% (0.0005 moles) was loaded into a glass flask equipped with a reflux condenser, heating mantle, and nitrogen inlet port. The initial chloride level was determined to be 19,339 ppm by KOH titration using bromcresol purple (BCP) as an indicator. Based on the acidity results, the mixture was treated with a mixture comprising 0.02 parts methanol (0.0005 moles) and 0.05 parts trimethyl orthoformate (0.0005 moles). The amount of trimethyl orthoformate present was the equivalent stoichiometric amount required to completely react the total residual chloride present. The mixture comprising methanol and trimethyl orthoformate was added through an additional funnel in 0.02 part incremental intervals as the mixture comprising cyclohexylmethyldimethoxysilane was heated to about 80° C. to 85° C. Samples were taken at 1 hour intervals and the chloride level determined by KOH titration using BCP as an indicator. The residual chloride level decreased from 19,339 ppm to 13,777 ppm in 5 hours.

We claim:

1. A method of preparing an alkoxysilane having reduced halide content comprising
   (a) contacting a mixture comprising an alkoxysilane described by formula $R_aH_bSi(OR^1)_{(4-a-b)}$, and residual halide with a mixture comprising about 1.5 to 15 moles of an alkyl alcohol per mole of residual halide, the alkyl alcohol comprising 1 to about 4 carbon atoms and about 0.1 to 5 moles of an orthoformate described by formula $HC(OR^1)_3$ per mole of residual halide, where each R is independently selected from the group consisting of substituted and unsubstituted hydrocarbon groups comprising 1 to about 20 carbon atoms, each $R^1$ is an independently selected hydrocarbon group comprising 1 to 4 carbon atoms, a=0, 1, 2, or 3, b=0, 1, 2, or 3, and a+b=0 to 3, to form mixture comprising additional alkoxysilane and lower boiling species, and
   (b) separating the lower boiling species and the alkoxysilane.

2. A method according to claim 1, where the lower boiling species including residual halide are contacted with a metal alkoxide.

3. A method according to claim 2, where the metal alkoxide is sodium methoxide.

4. A method according to claim 2, where the metal alkoxide is sodium ethoxide.

5. A method according to claim 1, where the residual halide is chloride.

6. A method according to claim 1, where the alkoxysilane is dicyclopentyldimethoxysilane.

7. A method according to claim 1, where the alkoxysilane is cyclohexylmethyldimethoxysilane.

8. A method according to claim 1, where the mixture comprises about 2.5 to 10 moles of an alkyl alcohol comprising 1 to about 4 carbon atoms per mole of residual halide.

9. A method according to claim 1, where the mixture comprises about 3.5 to 7 moles of an alkyl alcohol comprising 1 to about 4 carbon atoms per mole of residual halide.

10. A method according to claim 1, where the alkyl alcohol is methanol.

11. A method according to claim 1, where the alkyl alcohol is ethanol.

12. A method according to claim 1, where the mixture comprises about 0.5 to 2 moles of orthoformate per mole of residual halide.

13. A method according to claim 1, where the mixture comprises a stoichiometric amount of orthoformate per mole of residual halide.

14. A method according to claim 1, where the orthoformate is methyl orthoformate.

15. A method according to claim 1, where the orthoformate is ethyl orthoformate.

16. A method according to claim 1, where the weight percent of the orthoformate in alkyl alcohol is in the range of about 10 to 60 weight percent.

17. A method according to claim 1, where the weight percent of the orthoformate in alkyl alcohol is in the range of about 20 to 50 weight percent.

18. A method according to claim 1, where the weight percent of the orthoformate in alkyl alcohol is in the range of about 25 to 30 weight percent.

19. A method according to claim 1, where the lower boiling species and the alkoxysilane are separated by distillation.

20. A method of preparing an alkoxysilane having reduced halide content comprising (a) contacting a mixture comprising an alkoxysilane described by formula $R_aH_bSi(OR^1)_{(4-a-b)}$, and residual halide with a mixture comprising about 1.5 to 15 moles of an alkyl alcohol per mole of residual halide, the alkyl alcohol comprising 1 to about 4 carbon atoms and about 0.1 to 5 moles of an orthoformate described by formula $HC(OR^1)_3$ per mole of residual halide, where each R is independently selected from the group consisting of substituted and unsubstituted hydrocarbon groups comprising 1 to about 20 carbon atoms, each $R^1$ is an independently selected hydrocarbon group comprising 1 to 4 carbon atoms, a=0, 1, 2, or 3, b=0, 1, 2, or 3, and a+b=0 to 3, to form mixture comprising additional alkoxysilane and lower boiling species, and (b) contacting any remaining residual halide with a metal alkoxide, and (c) separating the lower boiling species and the alkoxysilane.

* * * * *